(12) United States Patent
Black

(10) Patent No.: US 6,912,480 B2
(45) Date of Patent: Jun. 28, 2005

(54) METHOD AND APPARATUS FOR DETERMINING THE MASS FLOW THROUGH AN ENGINE

(75) Inventor: John D Black, Ashbourne (GB)

(73) Assignee: Rolls-Royce, PLC, London (GB)

( * ) Notice: Subject to any disclaimer, the term of this patent is extended or adjusted under 35 U.S.C. 154(b) by 0 days.

(21) Appl. No.: 10/765,973

(22) Filed: Jan. 29, 2004

(65) Prior Publication Data
US 2004/0182143 A1 Sep. 23, 2004

(30) Foreign Application Priority Data
Feb. 18, 2003 (GB) .............................................. 0303639

(51) Int. Cl.[7] .............................................. G06F 16/00
(52) U.S. Cl. ..................... 702/183; 73/118.1; 73/118.2; 431/12
(58) Field of Search ........................... 73/118.1, 118.2; 702/183; 431/12

(56) References Cited

U.S. PATENT DOCUMENTS 4,121,455 A    10/1978  Haslett et al.
5,599,179 A *   2/1997  Lindner et al. ................ 431/12
6,364,602 B1 *  4/2002  Andrew et al. ................. 415/1
6,522,994 B1 *  2/2003  Lang ........................... 702/183

FOREIGN PATENT DOCUMENTS

EP          0 067 545 A3    12/1982

* cited by examiner

Primary Examiner—John Barlow
Assistant Examiner—Stephen J. Cherry
(74) Attorney, Agent, or Firm—Oliff & Berridge, PLC

(57) ABSTRACT

A method for determining the total mass flow through an engine (10) comprises measuring (32) the fuel flow to the engine (10) and measuring the concentration of carbon dioxide in the gases exhausted (22) from the engine (10). The concentration of carbon dioxide is measured by detecting the infrared radiation absorption spectrum of carbon dioxide using a laser (38) and a detector (46). The method comprises determining (48) the air to fuel ratio in the engine (10) from the fuel flow and the concentration of carbon dioxide. The method comprises determining (48) the air mass flow through the engine (10) from the air to fuel ratio and calculating (48) the total air and fuel mass flow through the engine (10) by adding the air mass flow through the engine (10) to the fuel mass flow to the engine (10).

28 Claims, 3 Drawing Sheets

METHOD AND APPARATUS FOR DETERMINING THE MASS FLOW THROUGH AN ENGINE

BACKGROUND AND SUMMARY

The present invention relates to a method and apparatus for determining the mass flow through an engine, the present invention relates in particular to a method and apparatus for determining the mass flow through a gas turbine engine.

There is a requirement for determining the total mass flow through the core engine of a gas turbine engine. The fuel flow to a gas turbine engine is already measured, but the airflow through the gas turbine engine is difficult to measure.

Accordingly the present invention seeks to provide a novel method and apparatus, which reduces, preferably overcomes, the above-mentioned problems.

Accordingly the present invention provides a method for determining the total mass flow through an engine comprising measuring the fuel flow to the engine, measuring the concentration of carbon dioxide, measuring the ratio of water to oxygen, measuring the ratio of carbon dioxide to oxygen or measuring the ratio of water to carbon dioxide in the gases exhausted in the engine from the fuel flow and the concentration of carbon dioxide, the ratio of water to oxygen, the ratio of carbon dioxide to oxygen or the ratio of water to carbon dioxide, determining the air mass flow through the engine from the air to fuel ratio and calculating the total air and fuel mass flow through the engine by adding the air mass flow through the engine to the fuel mass flow to the engine.

Measuring the concentration of carbon dioxide may comprise detecting infrared radiation emitted by carbon dioxide in the gases exhausted from the engine and determining the concentration of carbon dioxide.

Preferably measuring the concentration of carbon dioxide comprises detecting infrared radiation absorbed by carbon dioxide in the gases exhausted from the engine and determining the concentration of carbon dioxide.

Preferably measuring the ratio of water to oxygen comprises detecting infra-red radiation absorbed by water in the gases exhausted from the engine, detecting near infra-red radiation absorbed by oxygen in the gases exhausted from the engine, determining the concentration of water, determining the concentration of oxygen and calculating the ratio of water to oxygen.

Preferably measuring the ratio of carbon dioxide to oxygen comprises detecting infra-red radiation absorbed by carbon dioxide in the gases exhausted from the engine, detecting near infra-red radiation absorbed by oxygen in the gases exhausted from the engine, determining the concentration of carbon dioxide, determining the concentration of oxygen and calculating the ratio of carbon dioxide to oxygen.

Preferably measuring the ratio of water to carbon dioxide comprises detecting infrared radiation absorbed by water in the gases exhausted from the engine, detecting infrared radiation absorbed by carbon dioxide in the gases exhausted from the engine, determining the concentration of water, determining the concentration of carbon dioxide and calculating the ratio of water to carbon dioxide.

Preferably the method comprises irradiating the gases exhausted from the engine with a light.

Preferably the method comprises irradiating the gases exhausted from the engine with a laser light.

Preferably the method comprises detecting infrared radiation absorbed or emitted by the gases exhausted from the engine at a plurality of lines across the exhaust of the engine.

The method may comprise moving a detector. The method may comprise moving a light source.

Alternatively the method comprises moving at least one mirror.

Preferably the engine is a gas turbine engine. More preferably the engine is a turbofan gas turbine engine.

Accordingly the present invention also provides an apparatus for determining the total mass flow through an engine comprising means for measuring the fuel flow to the engine, means for measuring the concentration of carbon dioxide, means for measuring the ratio of water to oxygen, means for measuring the ratio of carbon dioxide to oxygen or means for measuring the ratio of water to carbon dioxide in the gases exhausted from the engine, means for determining the air to fuel ratio in the engine from the fuel flow and the concentration of carbon dioxide, the ratio of water to oxygen, the ratio of carbon dioxide to oxygen or the ratio of water to carbon dioxide, means for determining the air mass flow through the engine from the air to fuel ratio and means for calculating the total air and fuel mass flow through the engine by adding the air mass flow through the engine to the fuel mass flow to the engine.

Preferably the engine is a gas turbine engine. More preferably the gas turbine engine is a turbofan gas turbine engine.

Preferably the means for measuring the concentration of carbon dioxide comprises at least one detector. Preferably the detector comprises a spectrometer and a photo-detector, the spectrometer is optically coupled to the photo-detector. Preferably the spectrometer is a Fourier transform spectrometer.

Preferably the means for measuring the concentration of carbon dioxide comprises a light source. Preferably the light source is a laser. The laser may be a tunable laser. Preferably the laser is a diode laser. There may be a plurality of lasers. The lasers may be tuned to different wavelengths, there are means to switch the lasers on sequentially.

Preferably there are means to scan the gases exhausted from the engine. The means to scan may comprise one or more mirrors.

BRIEF DESCRIPTION OF THE DRAWINGS

The present invention will be more fully described by way of example with reference to the accompanying drawings in which.

DETAILED DESCRIPTION OF EMBODIMENTS

Figure 1:
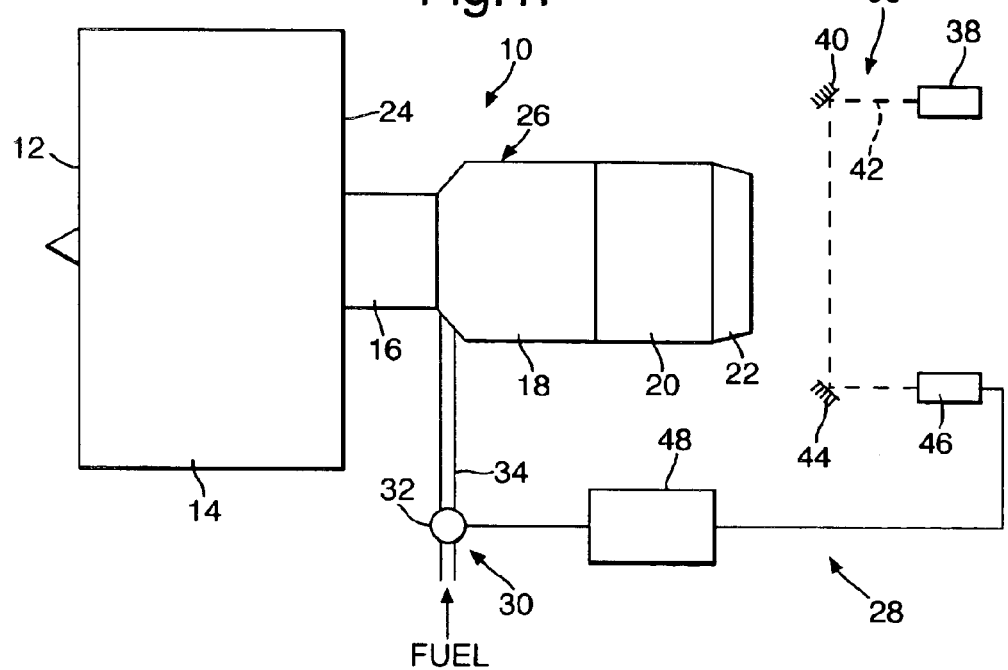
FIG. 1 shows a turbofan gas turbine engine having means for determining the total mass flow through an engine according to the present invention.

If the total concentration of carbon containing species, carbon dioxide, carbon monoxide, carbon and unburned hydrocarbon, or water in a core exhaust of a gas turbine engine is measured, then the total mass flow can be calculated provided the empirical formula of the hydrocarbon fuel is known.

A generalised equation for complete combustion of a hydrocarbon fuel with excess air, the process which always occurs in a gas turbine engine, is as follows:

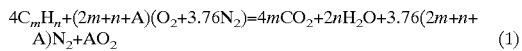

$$4C_mH_n+(2m+n+A)(O_2+3.76N_2)=4mCO_2+2nH_2O+3.76(2m+n+A)N_2+AO_2 \quad (1)$$

where the fuel is approximated by the empirical formula $C_mH_n$ and A is the number of molecules of excess air per molecule of hydrocarbon fuel. Excess air in this case includes air used for cooling components, which does not pass through the combustion section of the engine.

Substitution in the right hand side of the above equation (1) gives:

$$X_{CO2}=2m/(2.88(2m+n)+A)$$

where $X_{CO2}$ is the mole fraction of carbon dioxide.

If the composition of the hydrocarbon fuel, and hence the values of m and n are accurately determined, then the core mass flow can be found from $X_{CO2}$. At any given pressure and temperature, 1 mole (molecular weight in grams= Avogadro's number of molecules) of any pure gaseous substance occupies the same volume. Hence, the mole fraction of a species is equivalent to volume fraction, which is in turn proportional to the number of molecules per unit volume, in a gas mixture. This method assumes that combustion efficiency is 100%, i.e. all the carbon in the hydrocarbon fuel is converted into carbon dioxide. This is a good approximation, particularly at high power conditions.

From the above equation (1) it can be seen that the ratios of mole fractions are as follows:

$$X_{H2O}/X_{O2}=2n/A, X_{CO2}/X_{O2}=4m/A \text{ and } X_{H2O}/X_{CO2}=n/2m$$

Water is the only hydrogen containing combustion product, although when combustion is inefficient, the presence of unburned hydrocarbon may introduce small errors in mass flow based on water concentration measurement. There is an appreciable concentration of water vapour in the atmosphere and allowance is made for this, based on its measurement at the time of test. Water may condense in the engine intake under some atmospheric conditions causing the air entering the core engine to be drier than atmospheric air and allowance is made for this.

With carbon dioxide there is no problem of fluctuating atmospheric concentrations, but there is a small dependence on combustion efficiency, because all the carbon in the hydrocarbon fuel may not be converted to carbon dioxide. The $X_{H2O}/X_{CO2}$ ratio after correction for ambient humidity may be smaller than n/2m due to intake water condensation, or it may be larger than n/2m due to combustion inefficiency. Both these effects may compete. If the composition of the hydrocarbon fuel, and hence the values of m and n are accurately determined, then the core mass flow can be found from $X_{CO2}/X_{O2}$, $X_{H2O}/X_{O2}$ and $X_{H2O}/X_{CO2}$ ratios.

A turbofan gas turbine engine 10, as shown in FIG. 1, comprises in axial flow series an inlet 12, a fan section 14, a compressor section 16, a combustion section 18, a turbine section 20 and a core exhaust 22. The fan section 14 has a fan exhaust 24. The compressor section 16, the combustion section 18, the turbine section 20 and the exhaust 22 form the core engine 26 of the turbofan gas turbine engine 10.

Figure 2:
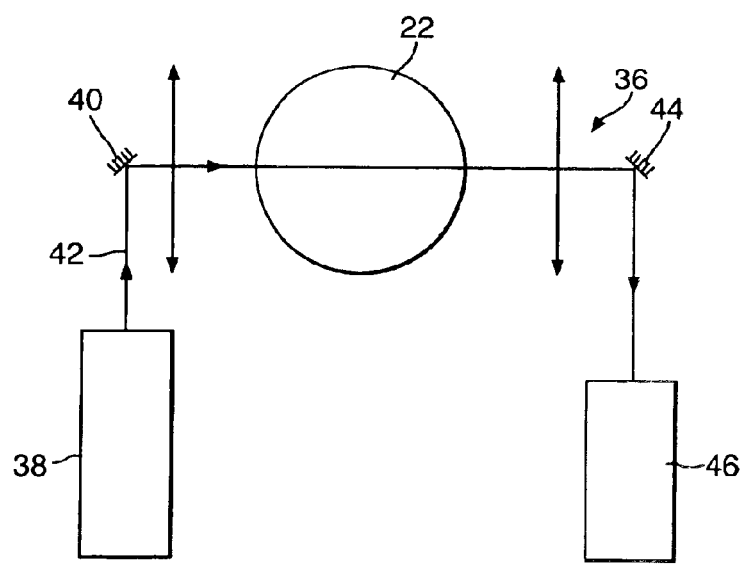
FIG. 2 is an enlarged view of a means for determining the total mass flow though an engine according to the present invention.

There are also means 28 for determining the total mass flow through the core engine 26 of the turbofan gas turbine engine 10 as shown in FIGS. 1 and 2. The means 28 for determining the total mass flow through the core engine 26 of the turbofan gas turbine engine 10 comprises means 30 to measure the fuel flow to the combustion section 18 of the turbofan gas turbine engine 10. The means 30 for measuring the fuel flow to the combustion section 18 comprises a fuel meter 32 arranged in a pipe 34 supplying fuel to the combustion section 18.

The means 28 for determining the total mass flow through the core engine 26 of the turbofan gas turbine engine 10 comprises means 36 for measuring the concentration of carbon dioxide in the exhaust gases leaving the exhaust 22 of the core engine 26 of the turbofan gas turbine engine 10. The means 36 for determining the concentration of carbon dioxide in the exhaust gases leaving the exhaust 22 of the core engine 26 of the turbofan gas turbine engine 10 comprises a tunable laser 38 and a first mirror 40 to direct a laser beam 42 through the exhaust gases leaving the exhaust 22 and a second mirror 44 to direct the laser beam 42, after passing through the exhaust gases leaving the exhaust 22, to a detector 46. The mirrors 40 and 44 are movable to allow the laser beam 42 to be scanned across at least a sufficient number of lines of sight such that substantially the whole of the cross-sectional area of the exhaust 22 is scanned so that an average measurement of the concentration is produced. There are means 48 to calculate the concentration of the carbon dioxide from the signal produced by the detector 46.

The means 28 for determining the total mass flow through the core engine 26 of the turbofan gas turbine engine 10 comprises means 48 for determining the air to fuel ratio in the engine from the fuel flow and the concentration of carbon dioxide. The means 28 for determining the total mass flow through the core engine 26 of the turbofan gas turbine engine 10 comprises means 48 for determining the air mass flow through the core engine 26 of the turbofan gas turbine engine 10 from the air to fuel ratio and there are means 48 for calculating the total air and fuel mass flow through the core engine 26 of the turbofan gas turbine engine 10 by adding the air mass flow through the core engine 26 of the turbofan gas turbine engine 10 to the fuel mass flow to the combustion section 18 of the turbofan gas turbine engine 10. The means 48 may be a computer or personal computer etc.

A method for determining the total mass flow through the core engine 26 of the turbofan gas turbine engine 10 is to measure the absolute carbon dioxide concentration in the exhaust gases leaving the exhaust 22 of the core engine 26 of the turbofan gas turbine engine 10. The absolute carbon dioxide concentration is measured using absorption spectroscopy, in which radiation absorbed by the carbon dioxide in the field of view of a detector 46 is measured. The detector 46 is a spectrometer, which is optically coupled to a photo-detector, preferably the spectrometer is a Fourier transform spectrometer. Alternatively the detector 46 may be a wavelength selecting filter optically coupled to a photo-detector. Carbon dioxide has many absorption lines in the infrared region. The field of view of the detector 46 is scanned across the whole of the exhaust 22 of the core engine 26 of the turbofan gas turbine engine 10 so that the average carbon dioxide concentration is determined, as shown in FIGS. 1 and 2. The tunable laser 38 limits the field of view of the detector 46 and provides good accuracy. Other light sources besides a laser may be used to produce the absorption spectrum.

Each line of sight of the detector 46 comprises a plurality of points through the exhaust gases and each point is at a different temperature and therefore the measured carbon dioxide absorption spectrum at each position is different. The measured carbon dioxide absorption spectrum for each point is compared to a plurality of calculated simulated carbon dioxide absorption spectra to find a match. The calculated simulated carbon dioxide absorption spectra correspond to different temperatures and the amplitude of the peaks in the calculated simulated carbon dioxide absorption spectra indicate the concentration of the carbon dioxide. The concentration of carbon dioxide at each point is determined by comparing the amplitude of the peaks in the measured carbon dioxide spectrum and the matched calculated simulated carbon dioxide spectrum and scaled accordingly. The carbon dioxide concentrations at all the points in a line of sight and for all the lines of sight are added together to produce an average carbon dioxide concentration.

The carbon dioxide spectrum depends upon the temperature profile of the exhaust gases leaving the exhaust 22 of the core engine 26 of the turbofan gas turbine engine 10. The temperature of the exhaust gases leaving the exhaust 22 of the core engine 26 of the turbofan gas turbine engine 10 is determined by monitoring the carbon dioxide absorption spectrum at different wavelengths of the carbon dioxide spectrum, in the laser case, by switching the laser wavelength between different regions of the absorption spectrum and keeping a single detector 46, thus by looking for absorption peaks at different wavelengths.

Figure 3:
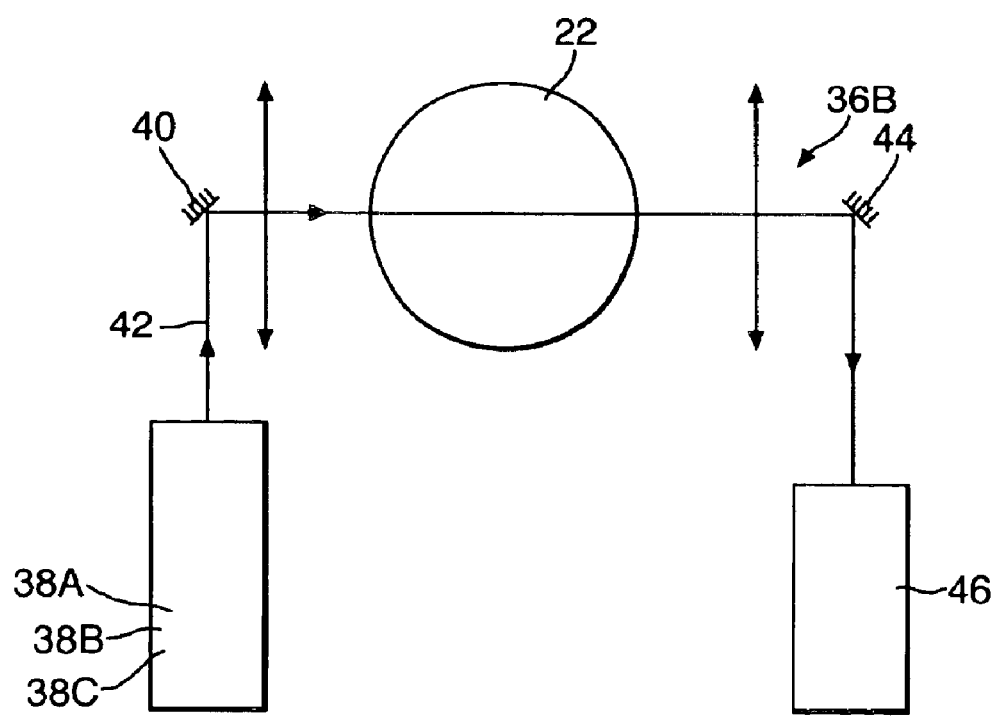
FIG. 3 is an enlarged view of an alternative means for determining the total mass flow though an engine according to the present invention.

A further means for determining the total mass flow through the core engine 26 of the turbofan gas turbine engine 10 as shown in FIGS. 1 and 3. The means 28B for determining the total mass flow through the core engine 26 of the turbofan gas turbine engine 10 comprises means 30 to measure the fuel flow to the combustion section 18 of the turbofan gas turbine engine 10. The means 30 for measuring the fuel flow to the combustion section 18 comprises a fuel meter 32 arranged in a pipe 34 supplying fuel to the combustion section 18.

The means 28B for determining the total mass flow through the core engine 26 of the turbofan gas turbine engine 10 comprises means 36B for determining the ratio of water to oxygen, the ratio of carbon dioxide to oxygen or the ratio of water to carbon dioxide in the exhaust gases leaving the exhaust 22 of the core engine 26 of the turbofan gas turbine engine 10. The means 36 for determining the ratio of water to oxygen, the ratio of carbon dioxide to oxygen or the ratio of water to carbon dioxide in the exhaust gases leaving the exhaust 22 of the core engine 26 of the turbofan gas turbine engine 10 comprises three lasers 38A, 38B and 38C and a first mirror 40 to direct a laser beam 42 through the exhaust gases leaving the exhaust 22 and a second mirror 44 to direct the laser beam 42, after passing through the exhaust gases leaving the exhaust 22, to a detector 46. The mirrors 40 and 44 are movable to allow the laser beam 42 to be scanned across at least a sufficient number of lines of sight such that substantially the whole of the cross-sectional area of the exhaust 22 is scanned so that an average measurement of the concentration is produced. The laser 38A is used to measure the concentration of carbon dioxide, the laser 38B is used to measure the concentration of oxygen and the laser 38C is used to measure the concentration of water. There are means 48 to determine the concentration of the carbon dioxide, the concentration of oxygen and the concentration of water from the signal produced by the detector 46. There are means 48 to determine the ratio of water to oxygen, the ratio of carbon dioxide to oxygen or the ratio of water to carbon dioxide from the concentrations of carbon dioxide, oxygen and water.

The means 28 for determining the total mass flow through the core engine 26 of the turbofan gas turbine engine 10 comprises means 48 for determining the air to fuel ratio in the engine from the fuel flow and the ratio of water to oxygen, the ratio of carbon dioxide to oxygen or the ratio of water to carbon dioxide. The means 28 for determining the total mass flow through the core engine 26 of the turbofan gas turbine engine 10 comprises means 48 for determining the air mass flow through the core engine 26 of the turbofan gas turbine engine 10 from the air to fuel ratio and there are means 48 for calculating the total air and fuel mass flow through the core engine 26 of the turbofan gas turbine engine 10 by adding the air mass flow through the core engine 26 of the turbofan gas turbine engine 10 to the fuel mass flow to the combustion section 18 of the turbofan gas turbine engine 10. The means 48 may be a computer or personal computer etc.

A method for determining the total mass flow through the core engine 26 of the turbofan gas turbine engine 10 is to measure the absolute carbon dioxide concentration, the absolute oxygen concentration and the absolute water concentration in the exhaust gases leaving the exhaust 22 of the core engine 26 of the turbofan gas turbine engine 10. The absolute carbon dioxide concentration, the absolute oxygen concentration and the absolute water concentration are measured using absorption spectroscopy, in which radiation absorbed by the carbon dioxide, water and oxygen in the field of view of a detector 46 is measured. Carbon dioxide and water have many absorption lines in the infrared region and oxygen has some weak absorption lines in the near infrared region around 763 nm. The detector 46 is a spectrometer, which is optically coupled to a photo-detector, preferably the spectrometer is Fourier transform spectrometer. Alternatively the detector may be a wavelength selecting filter optically coupled to a photo-detector. The field of view of the detector 46 is scanned across the whole of the exhaust 22 of the core engine 26 of the turbofan gas turbine engine 10 so that the average carbon dioxide concentration, the average oxygen concentration and average water concentration is determined, as shown in FIGS. 1 and 3. The lasers 38A, 38B and 38C limit the field of view of the detector 46 and provide good accuracy. Other light sources besides a laser may be used to produce the absorption spectrum. The laser beams from the lasers 38A, 38B and 38C are combined using dichroic optical elements and switching the lasers 38A, 38B and 38C on sequentially to allow the use of a single detector 46.

Each line of sight of the detector 46 comprises a plurality of points through the exhaust gases and each point is at a different temperature and therefore the measured carbon dioxide, oxygen and water absorption spectra at each position is different. The measured carbon dioxide absorption spectrum for each point is compared to a plurality of calculated simulated carbon dioxide absorption spectra to find a match. The calculated simulated carbon dioxide absorption spectra correspond to different temperatures and the amplitude of the peaks in the calculated simulated carbon dioxide absorption spectra indicate the concentration of the carbon dioxide. The concentration of carbon dioxide at each point is determined by comparing the amplitude of the peaks in the measured carbon dioxide spectrum and the matched calculated simulated carbon dioxide spectrum and scaled accordingly. The carbon dioxide concentrations at all the points in a line of sight and for all the lines of sight are added together to produce an average carbon dioxide concentration.

Similarly the measured oxygen absorption spectrum for each point is compared to a plurality of calculated simulated oxygen absorption spectra to find a match. The calculated simulated oxygen absorption spectra correspond to different temperatures and the amplitude of the peaks in the calculated simulated oxygen absorption spectra indicate the concentration of the oxygen. The concentration of oxygen at each point is determined by comparing the amplitude of the peaks in the measured oxygen spectrum and the matched calculated simulated oxygen spectrum and scaled accordingly. The oxygen concentrations at all the points in a line of sight and for all the lines of sight are added together to produce an average oxygen concentration.

Additionally the measured water absorption spectrum for each point is compared to a plurality of calculated simulated water absorption spectra to find a match. The calculated simulated water absorption spectra correspond to different temperatures and the amplitude of the peaks in the calculated simulated water absorption spectra indicate the concentration of the water. The concentration of water at each point is determined by comparing the amplitude of the peaks in the measured water spectrum and the matched calculated simulated water spectrum and scaled accordingly. The water concentrations at all the points in a line of sight and for all the lines of sight are added together to produce an average water concentration.

The carbon dioxide spectrum depends upon the temperature profile of the exhaust gases leaving the exhaust 22 of the core engine 26 of the turbofan gas turbine engine 10. The temperature of the exhaust gases leaving the exhaust 22 of the core engine 26 of the turbofan gas turbine engine 10 is determined by monitoring the carbon dioxide absorption spectrum at different wavelengths of the carbon dioxide spectrum by switching the laser 38A wavelength between different regions of the absorption spectrum and keeping a single detector 46, thus by looking for absorption peaks at different wavelengths.

Then a ratio of water to oxygen, a ratio of carbon dioxide to oxygen or water to carbon dioxide is determined.

Figure 4:
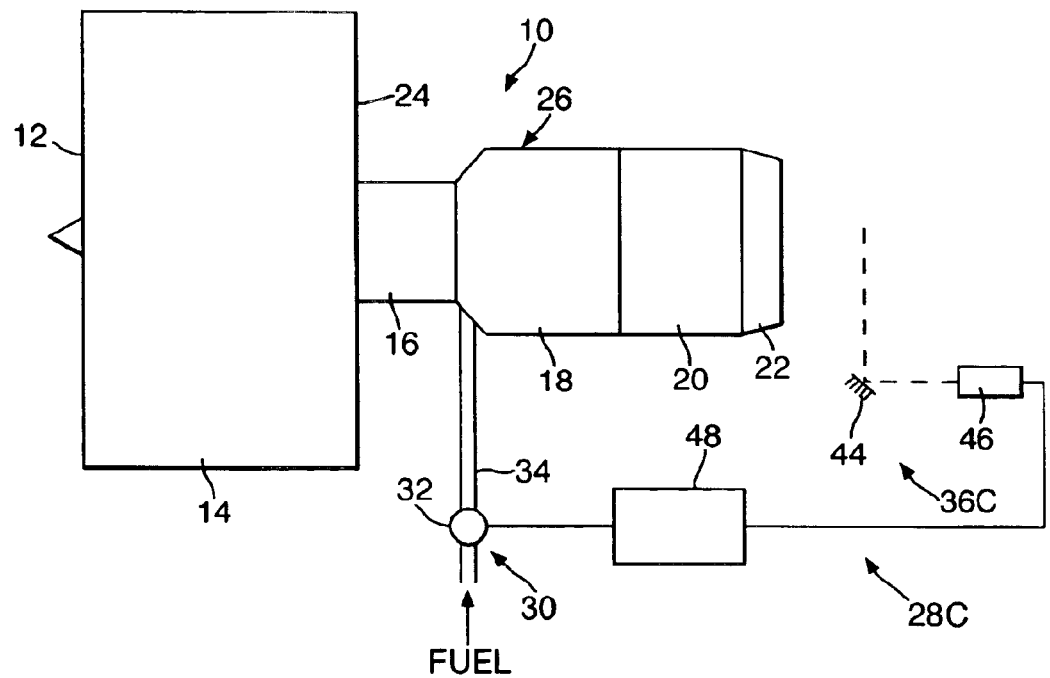
FIG. 4 shows a turbofan gas turbine engine having means for determining the total mass flow through an engine according to the present invention.

A turbofan gas turbine engine 10, as shown in FIG. 4, comprises in axial flow series an inlet 12, a fan section 14, a compressor section 16, a combustion section 18, a turbine section 20 and a core exhaust 22. The fan section 14 has a fan exhaust 24. The compressor section 16, the combustion section 18, the turbine section 20 and the exhaust 22 from the core engine 26 of the turbofan gas turbine engine 10.

Figure 5:
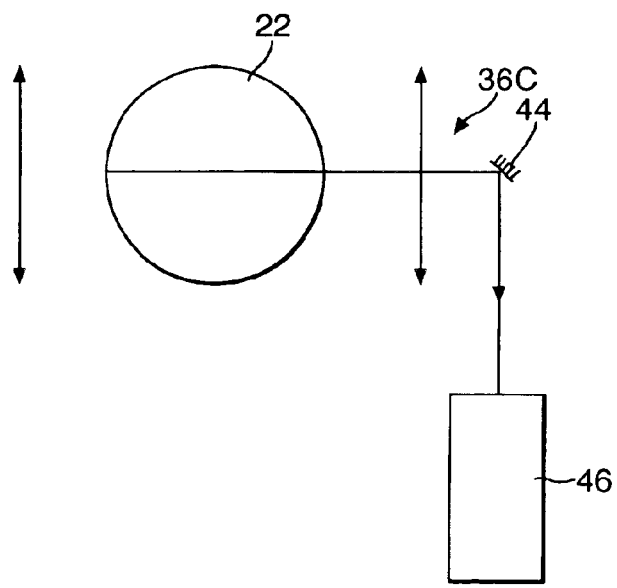
FIG. 5 is an enlarged view of a means for determining the total mass flow through an engine according the present invention.

There are also means 28C for determining the total mass flow through the core engine 26 of the turbofan gas turbine engine 10, as shown in FIGS. 4 and 5. The means 28C for determining the total mass flow through the core engine 26 of the turbofan gas turbine engine 10 comprises means 30 to measure the fuel flow to the combustion section 18 of the turbofan gas turbine engine 10. The means 30 for measuring the fuel flow to the combustion section 18 comprises a fuel meter 32 arranged in a pipe 34 supplying fuel to the combustion section 18.

The means 28C for determining the total mass flow through the core engine 26 of the turbofan gas turbine engine 10 comprises means 36C for measuring the concentration of carbon dioxide in the exhaust gases leaving the exhaust 22 of the core engine 26 of the turbofan gas turbine engine 10. The means 36C for determining the concentration of carbon dioxide in the exhaust gases leaving the exhaust 22 of the core engine 26 of the turbofan gas turbine engine 10 comprises a mirror 44 and a detector 46. The mirror 44 is movable to allow the detector 46 to be scanned across at least a sufficient number of lines of sight such that substantially the whole of the cross-sectional area of the exhaust 22 is scanned so that an average measurement of the concentration is produced. There are means 48 to calculate the concentration of the carbon dioxide from the signal produced by the detector 46.

The means 28C for determining the total mass flow through the core engine 26 of the turbofan gas turbine engine 10 comprises means 48 for determining the air to fuel ratio in the engine from the fuel flow and the concentration of carbon dioxide. The means 28C for determining the total mass flow through the core engine 26 of the turbofan gas turbine engine 10 comprises means 48 for determining the air mass flow through the core engine 26 of the turbofan gas turbine engine 10 from the air to fuel ratio and there are means 48 for calculating the total air and fuel mass flow through the core engine 26 of the turbofan gas turbine engine 10 by adding the air mass flow through the core engine 26 of the turbofan gas turbine engine 10 to the fuel mass flow to the combustion section 18 of the turbofan gas turbine engine 10. The means 48 may be a computer or personal computer etc.

A method for determining the total mass flow through the core engine 26 of the turbofan gas turbine engine 10 is to measure the absolute carbon dioxide concentration in the exhaust gases leaving the exhaust 22 of the core engine 26 of the turbofan gas turbine engine 10. The absolute carbon dioxide concentration is measured using a passive infrared system, in which radiation emitted by the carbon dioxide in the field of view of a detector 46 is spectrally filtered so that only carbon dioxide radiation, e.g. radiation in the infrared band around a wavelength of 4.3 $\mu$m, reaches the detector 46. The detector 46 is a spectrometer, which is optically coupled to a photo-detector and preferably the spectrometer is a Fourier transform spectrometer. The field of view of the detector 46 is scanned across the whole of the exhaust 22 of the core engine 26 of the turbofan gas turbine engine 10 so that the average carbon dioxide concentration is determined, as shown in FIGS. 4 and 5.

Each line of sight of the detector 46 comprises a plurality of points through the exhaust gases and each point is at a different temperature and therefore the measured carbon dioxide emission spectrum at each position is different. The measured carbon dioxide emission spectrum for each point is compared to a plurality of calculated simulated carbon dioxide emission spectra to find a match. The calculated simulated carbon dioxide emission spectra correspond to different temperatures and the amplitude of the peaks in the calculated simulated carbon dioxide emission spectra indicate the concentration of the carbon dioxide. The concentration of carbon dioxide at each point is determined by comparing the amplitude of the peaks in the measured carbon dioxide spectrum and the matched calculated simulated carbon dioxide spectrum and scaled accordingly. The carbon dioxide concentrations at all the points in a line of sight and for all the lines of sight are added together to produce an average carbon dioxide concentration.

The carbon dioxide spectrum depends upon the temperature profile of the exhaust gases leaving the exhaust 22 of the core engine 26 of the turbofan gas turbine engine 10. The temperature of the exhaust gases leaving the exhaust 22 of the core engine 26 of the turbofan gas turbine engine 10 is determined by monitoring the carbon dioxide emission spectrum at different wavelengths of the carbon dioxide spectrum by using one or more other detectors 46, thus by looking for emission peaks at different wavelengths.

The advantage of the present invention is that it does not require the use of any hardware attached to the engine or intruding into the gas path, and therefore it can be applied to any engine without affecting the performance of the engine. A further advantage of the present invention is that the measurement response times are potentially very fast, so that engine transient behaviour may be studied. The apparatus of the present invention may be small and lightweight. The present invention may form part of an engine health monitoring system.

Although the present invention has been described with reference to a gas turbine engine, the invention is equally applicable to other engines.

Although the present invention has been described with reference to the use of mirrors, they are not essential and it may be possible to move the detector and to move the light source.

Although the present invention has been described with reference to the use of the ratios of water to oxygen, carbon dioxide to oxygen or water to carbon dioxide it may be equally possible to use the inverse of these ratios.

What is claimed is:

1. A method for determining the total mass flow through an engine, comprising:
    measuring the fuel mass flow to the engine,
    measuring the concentration of carbon dioxide, measuring the ratio of water to oxygen, measuring the ratio of carbon dioxide to oxygen or measuring the ratio of water to carbon dioxide in the gases exhausted from the engine,
    determining the air to fuel ratio in the engine from the fuel mass flow and the concentration of carbon dioxide, the ratio of water to oxygen, the ratio of carbon dioxide to oxygen or the ratio of water to carbon dioxide,
    determining the air mass flow through the engine from the air to fuel ratio, and
    calculating the total air and fuel mass flow through the engine by adding the air mass flow through the engine to the fuel mass flow to the engine.

2. A method as claimed in claim 1 wherein measuring the concentration of carbon dioxide comprises detecting infra-red radiation emitted by carbon dioxide in the gases exhausted from the engine and determining the concentration of carbon dioxide.

3. A method as claimed in claim 1 wherein measuring the concentration of carbon dioxide comprises detecting infra-red radiation absorbed by carbon dioxide in the gases exhausted from the engine and determining the concentration of carbon dioxide.

4. A method as claimed in claim 1 wherein measuring the ratio of water to oxygen comprises detecting infra-red radiation absorbed by water in the gases exhausted from the engine, detecting near infra-red radiation absorbed by oxygen in the gases exhausted from the engine, determining the concentration of water, determining the concentration of oxygen and calculating the ratio of water to oxygen.

5. A method as claimed in claim 1 wherein measuring the ratio of carbon dioxide to oxygen comprises detecting infra-red radiation absorbed by carbon dioxide in the gases exhausted from the engine, detecting near infra-red radiation absorbed by oxygen in the gases exhausted from the engine, determining the concentration of carbon dioxide, determining the concentration of oxygen and calculating the ratio of carbon dioxide to oxygen.

6. A method as claimed in claim 1 wherein measuring the ratio of water to carbon dioxide comprises detecting infra-red radiation absorbed by water in the gases exhausted from the engine, detecting infra-red radiation absorbed by carbon dioxide in the gases exhausted from the engine, determining the concentration of water, determining the concentration of carbon dioxide and calculating the ratio of water to carbon dioxide.

7. A method as claimed in claim 1 comprises irradiating the gases exhausted from the engine with a light.

8. A method as claimed in claim 7 comprising irradiating the gases exhausted from the engine with a laser light.

9. A method as claimed in claim 1 comprising detecting infrared radiation absorbed or emitted by the gases exhausted from the engine at a plurality of lines across the exhaust of the engine.

10. A method as claimed in claim 9 comprising moving a detector.

11. A method as claimed in claim 9 comprising moving a light source.

12. A method as claimed in claim 9 comprising moving at least one mirror.

13. A method as claimed in claim 1 wherein the engine is a gas turbine engine.

14. A method as claimed in claim 13 wherein the engine is a turbofan gas turbine engine.

15. An apparatus for determining the total mass flow through an engine, comprising:
    means for measuring the fuel mass flow to the engine,
    means for measuring the concentration of carbon dioxide, means for measuring the ratio of water to oxygen, means for measuring the ratio of carbon dioxide to oxygen or means for measuring the ratio of water to carbon dioxide in the gases exhausted from the engine,
    means for determining the air to fuel ratio in the engine from the fuel mass flow and the concentration of carbon dioxide, the ratio of water to oxygen, the ratio of carbon dioxide to oxygen or the ratio of water to carbon dioxide,
    means for determining the air mass flow through the engine from the air to fuel ratio, and
    means for calculating the total air and fuel mass flow through the engine by adding the air mass flow through the engine to the fuel mass flow to the engine.

16. An apparatus as claimed in claim 15 wherein the engine is a gas turbine engine.

17. An apparatus as claimed in claim 16 wherein the gas turbine engine is a turbofan gas turbine engine.

18. An apparatus as claimed in claim 15 wherein the means for measuring the concentration of carbon dioxide comprises at least one detector.

19. An apparatus as claimed in claim 18 wherein the detector comprises a spectrometer and a photo-detector, the spectrometer is optically coupled to the photo-detector.

20. An apparatus as claimed in claim 19 wherein the spectrometer is a Fourier transform spectrometer.

21. An apparatus as claimed in claim 19 wherein the means for measuring the concentration of carbon dioxide comprises a light source.

22. An apparatus as claimed in claim 21 wherein the light source is a laser.

23. An apparatus as claimed in claim 22 wherein the laser is a tunable laser.

24. An apparatus as claimed in claim 22 wherein the laser is a diode laser.

25. An apparatus as claimed in claim 15 wherein there are means to scan the gases exhausted from the engine.

26. An apparatus as claimed in claim 25 wherein the means to scan comprises one or more mirrors.

27. An apparatus as claimed in claim 22 wherein there are a plurality of lasers.

28. An apparatus as claimed in claim 27 wherein the lasers are tuned to different wavelengths, there are means to switch the lasers on sequentially.

* * * * *